United States Patent [19]
Lange

[11] Patent Number: 6,071,395
[45] Date of Patent: Jun. 6, 2000

[54] PROCESS AND DEVICE FOR ISOLATING NUCLEIC ACIDS

[76] Inventor: Hans Lange, Romerstrabe 99D, 68623 Lampertheim, Germany

[21] Appl. No.: 09/142,958

[22] PCT Filed: Mar. 14, 1997

[86] PCT No.: PCT/DE97/00517

§ 371 Date: Jan. 25, 1999

§ 102(e) Date: Jan. 25, 1999

[87] PCT Pub. No.: WO97/34908

PCT Pub. Date: Sep. 25, 1997

[30] Foreign Application Priority Data

Mar. 15, 1996 [DE] Germany ............... 196 10 354

[51] Int. Cl.⁷ .................................................. B01D 61/42
[52] U.S. Cl. .................. 204/602; 210/450; 210/462; 210/465; 210/600; 210/513; 210/615; 422/69; 422/70; 536/25.4; 536/25.41; 536/25.42
[58] Field of Search ................... 536/25.4–25.42; 422/69, 70; 204/602; 210/450, 462, 465, 600, 673, 675

[56] References Cited

U.S. PATENT DOCUMENTS

| | | | |
|---|---|---|---|
| 3,706,381 | 12/1972 | Joynes et al. ................ | 210/198.2 |
| 3,969,218 | 7/1976 | Scott ............................ | 204/613 |
| 4,164,464 | 8/1979 | Allington et al. ............. | 204/600 |
| 4,222,836 | 9/1980 | Kerr et al. .................... | 204/468 |
| 4,459,198 | 7/1984 | Mizuno et al. ............... | 204/602 |
| 4,695,555 | 9/1987 | O'Keefe ....................... | 436/150 |
| 4,699,706 | 10/1987 | Burd et al. .................... | 204/613 |
| 4,708,782 | 11/1987 | Andreson et al. ............ | 204/198.2 |
| 4,861,555 | 8/1989 | Mowrey, Jr. .................. | 422/70 |
| 4,964,961 | 10/1990 | Brautigan et al. ............ | 204/183.2 |
| 5,151,165 | 9/1992 | Huynh .......................... | 204/615 |
| 5,340,452 | 8/1994 | Brenner et al. ............... | 204/180.1 |
| 5,453,382 | 9/1995 | Novotny et al. .............. | 204/542 |
| 5,569,365 | 10/1996 | Rabin et al. .................. | 204/450 |
| 5,849,166 | 12/1998 | Fuller ........................... | 204/468 |
| 5,860,642 | 11/1998 | Fuller ........................... | 435/6 |
| 5,874,213 | 2/1999 | Cummins et al. ............. | 435/6 |

FOREIGN PATENT DOCUMENTS

| | | |
|---|---|---|
| 0060082 | 9/1982 | European Pat. Off. . |
| 0555962 | 8/1993 | European Pat. Off. . |
| 0676643 | 4/1995 | European Pat. Off. . |
| 0687502 | 6/1995 | European Pat. Off. . |
| 3913814 | 7/1990 | Germany . |
| 0281354 | 8/1990 | Germany . |
| 9626234 | 1/1998 | Germany . |
| 9734908 | 9/1997 | WIPO . |

OTHER PUBLICATIONS

Tsuda, "Chromatographic Behavior in Electrochromatography," Anal. Chem., 60(17), 1677–1680 (Sep. 1, 1988).

Primary Examiner—Cecilia Tsang
Assistant Examiner—L. Eric Crane
Attorney, Agent, or Firm—Vanophem Meehan & Vanophem, P.C.

[57] ABSTRACT

Described is an apparatus for the contamination-free isolation of nucleic acids from biological fluids and suspensions containing nucleic acids comprising: a reaction compartment for holding an adsorption medium laden with nucleic acids; connected via a channel to a removal compartment; wherein the nucleic acids can be moved by an electrophoresis device from the reaction compartment into the removal compartment and enriched there; and the reaction compartment can be charged via a charging orifice and drained via a draining orifice being located essentially opposite of the charging orifice.

30 Claims, 16 Drawing Sheets

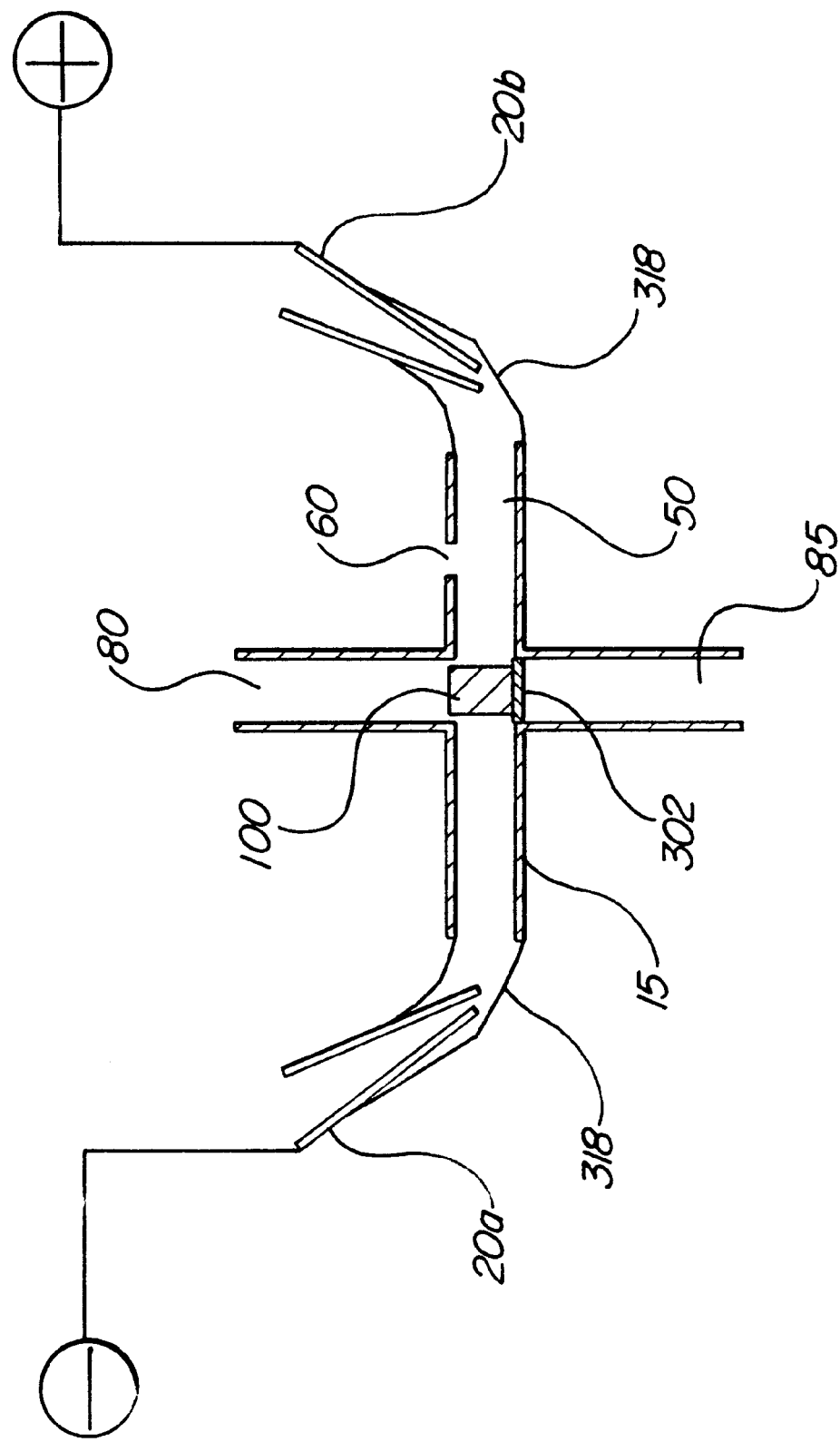

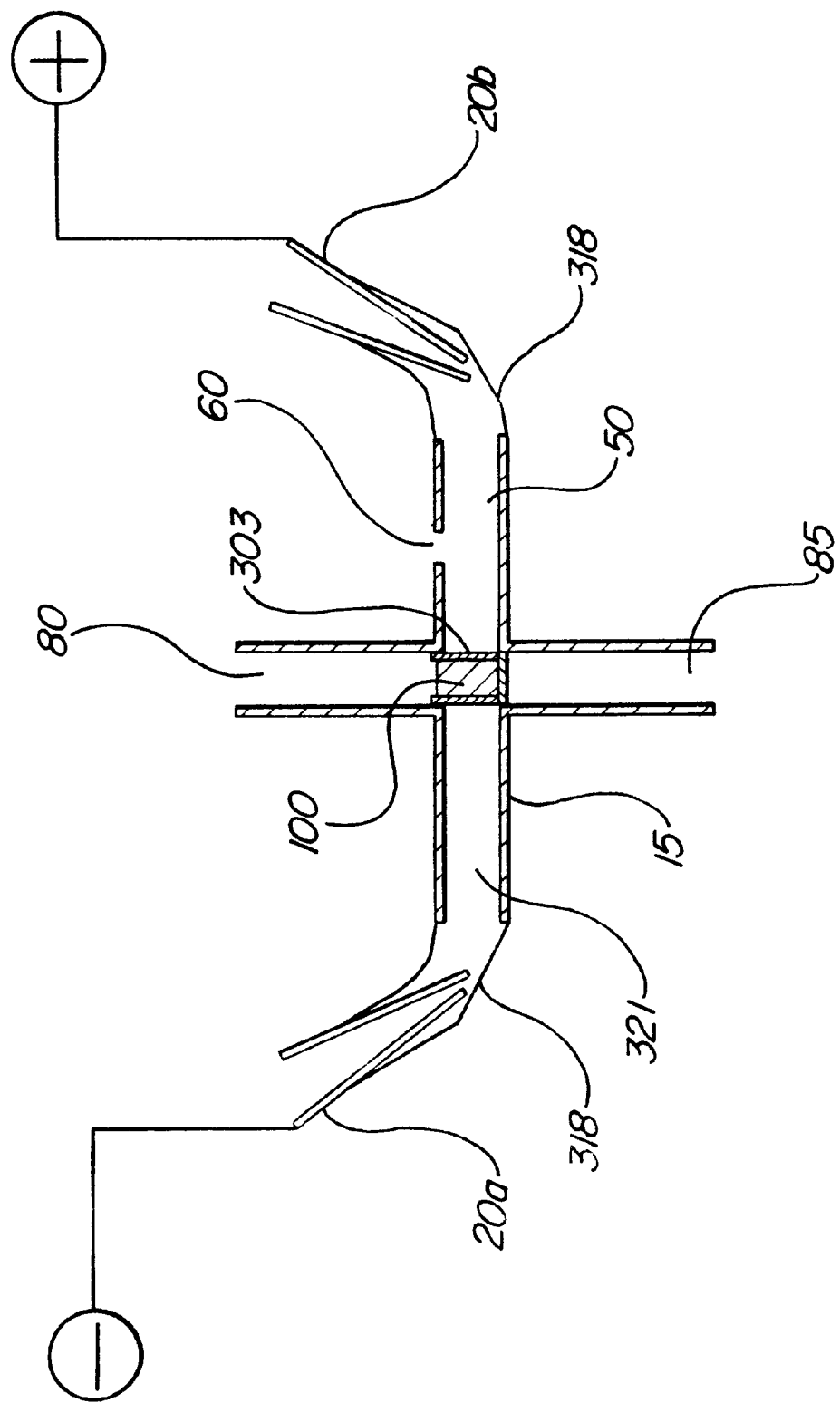

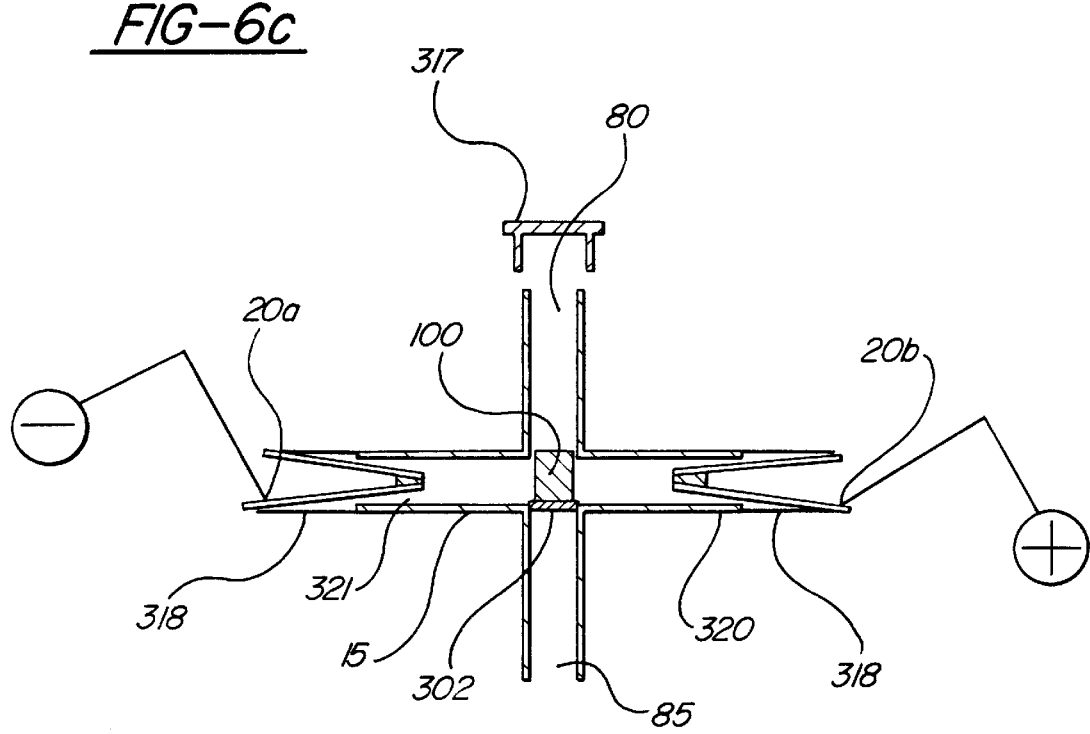

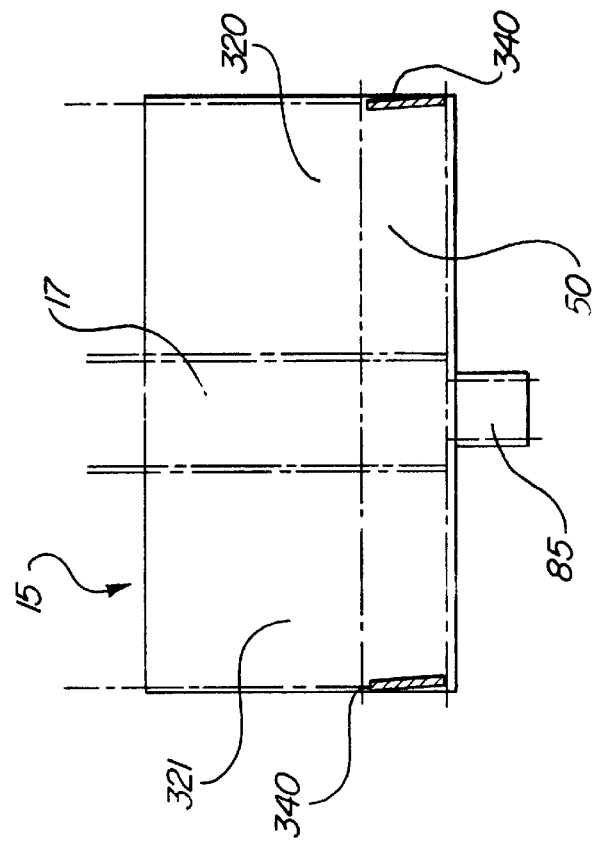
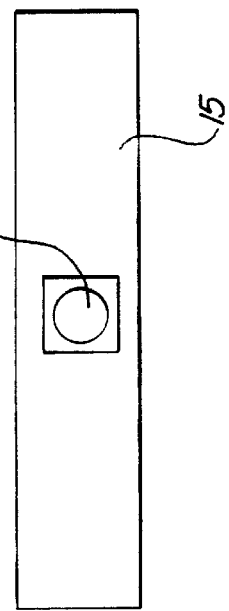
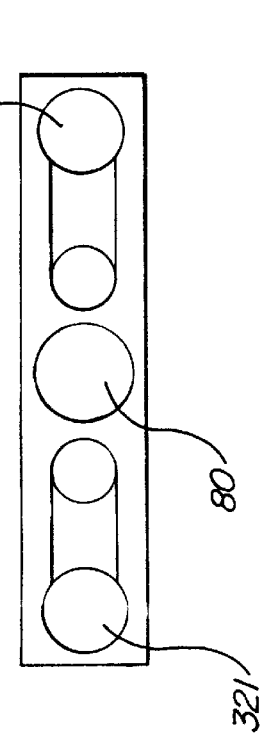

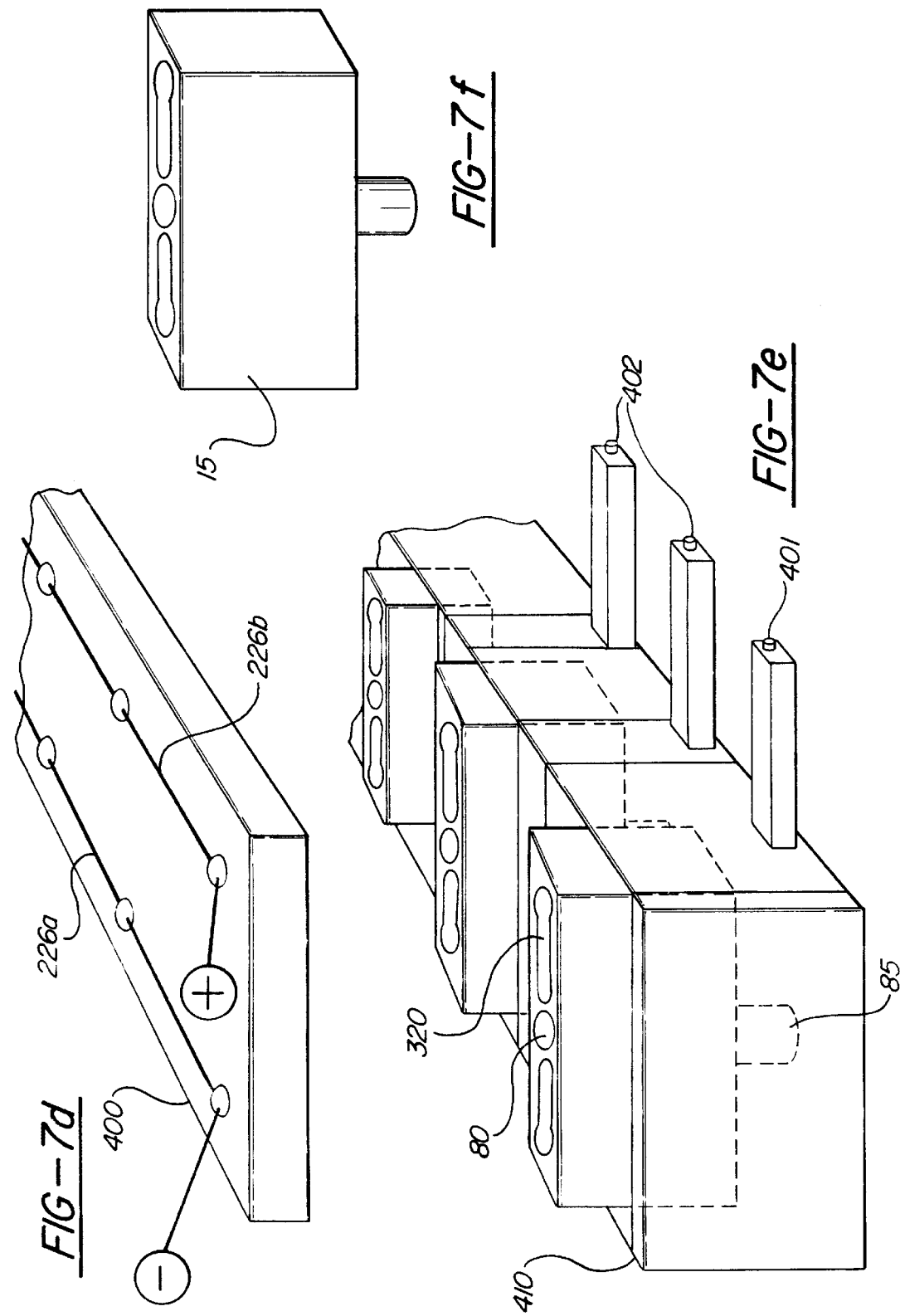

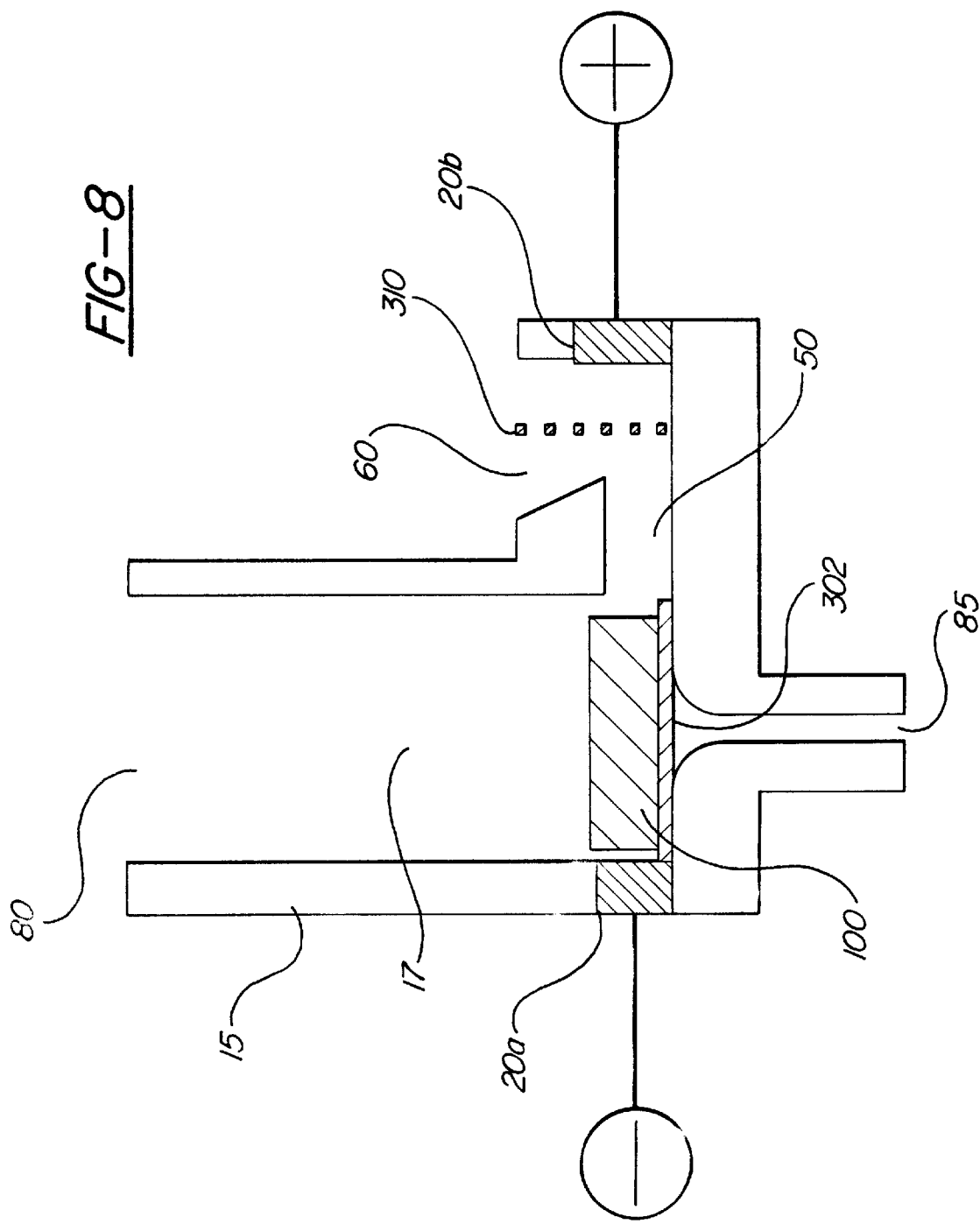

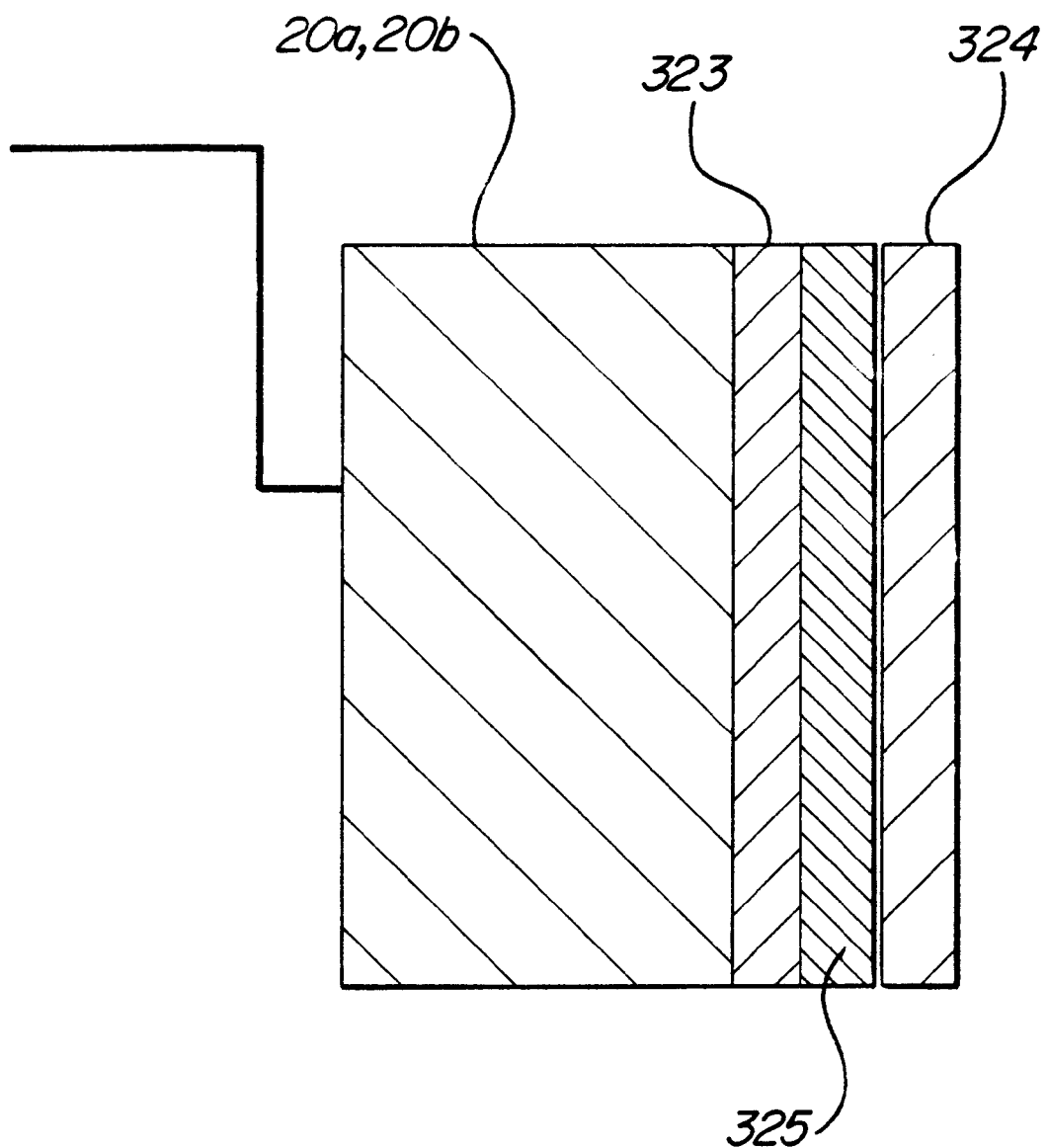

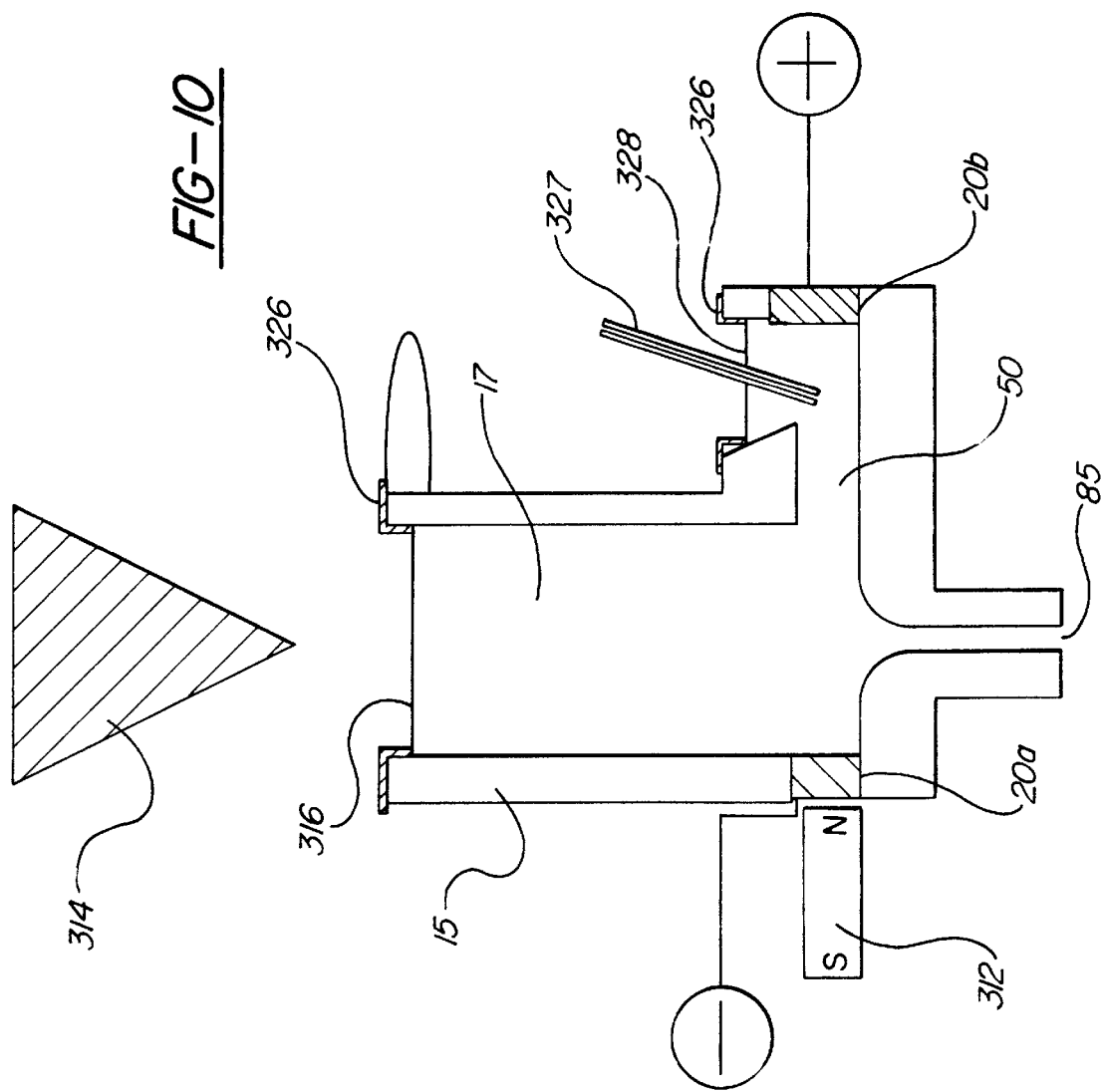

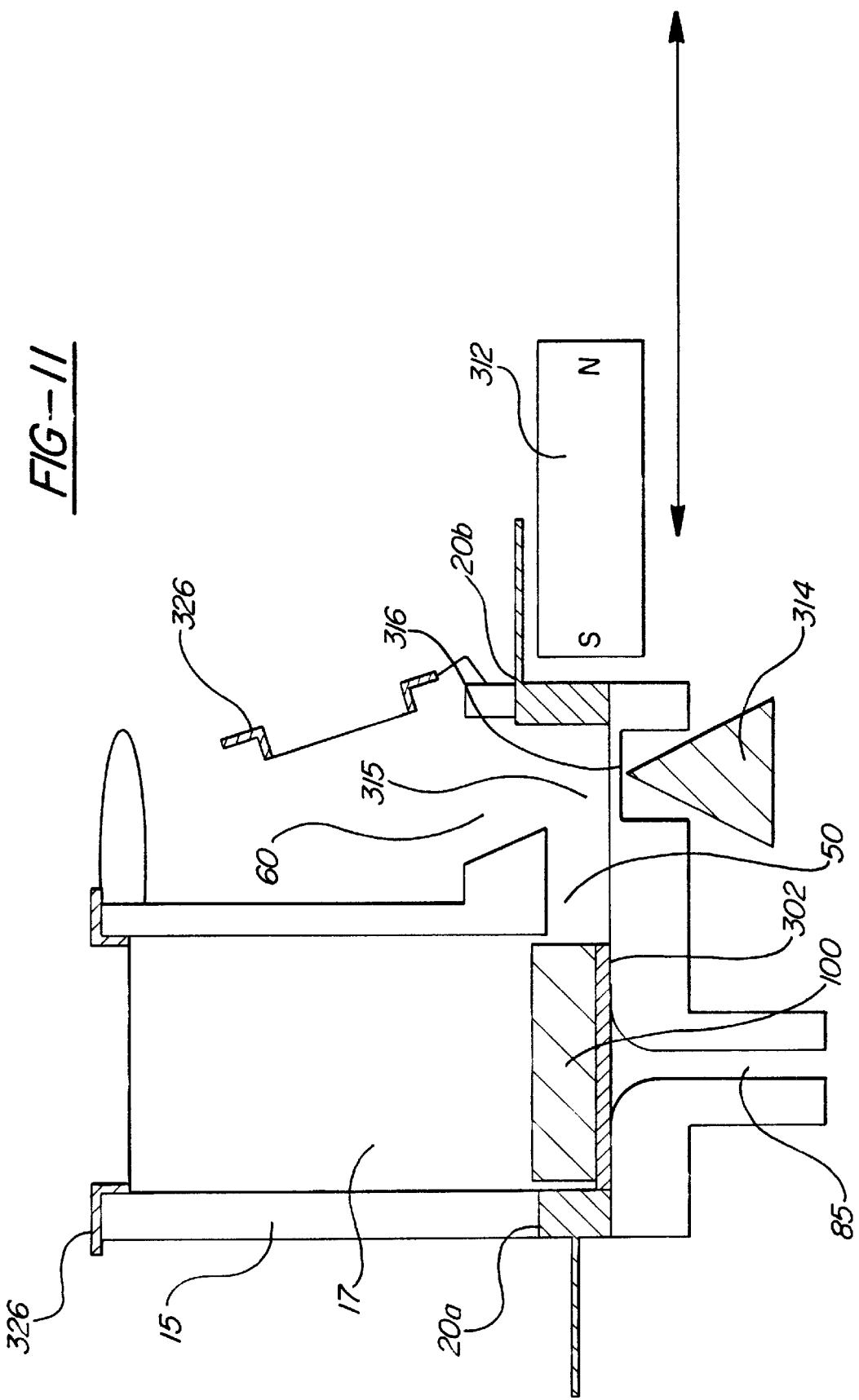

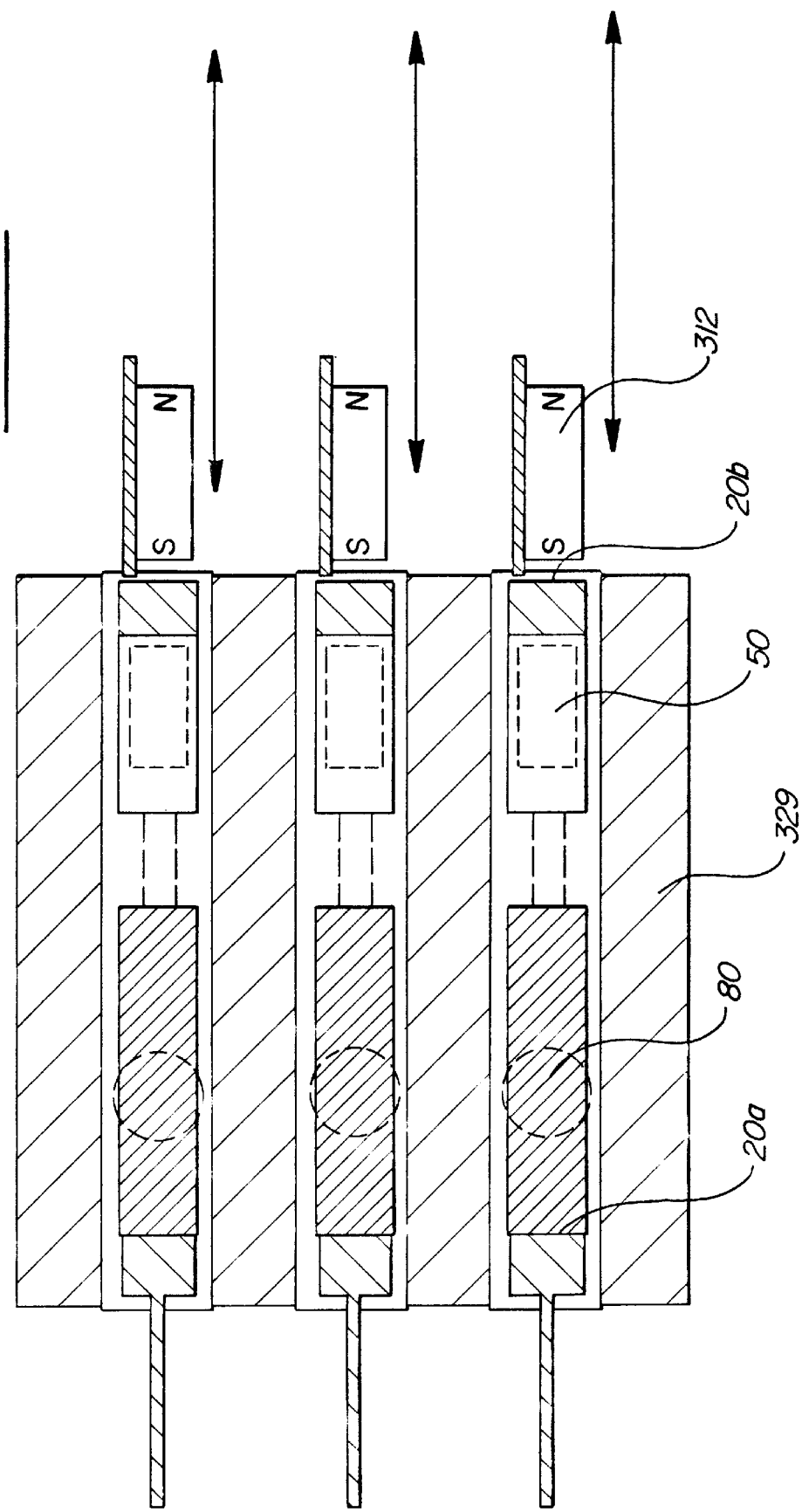

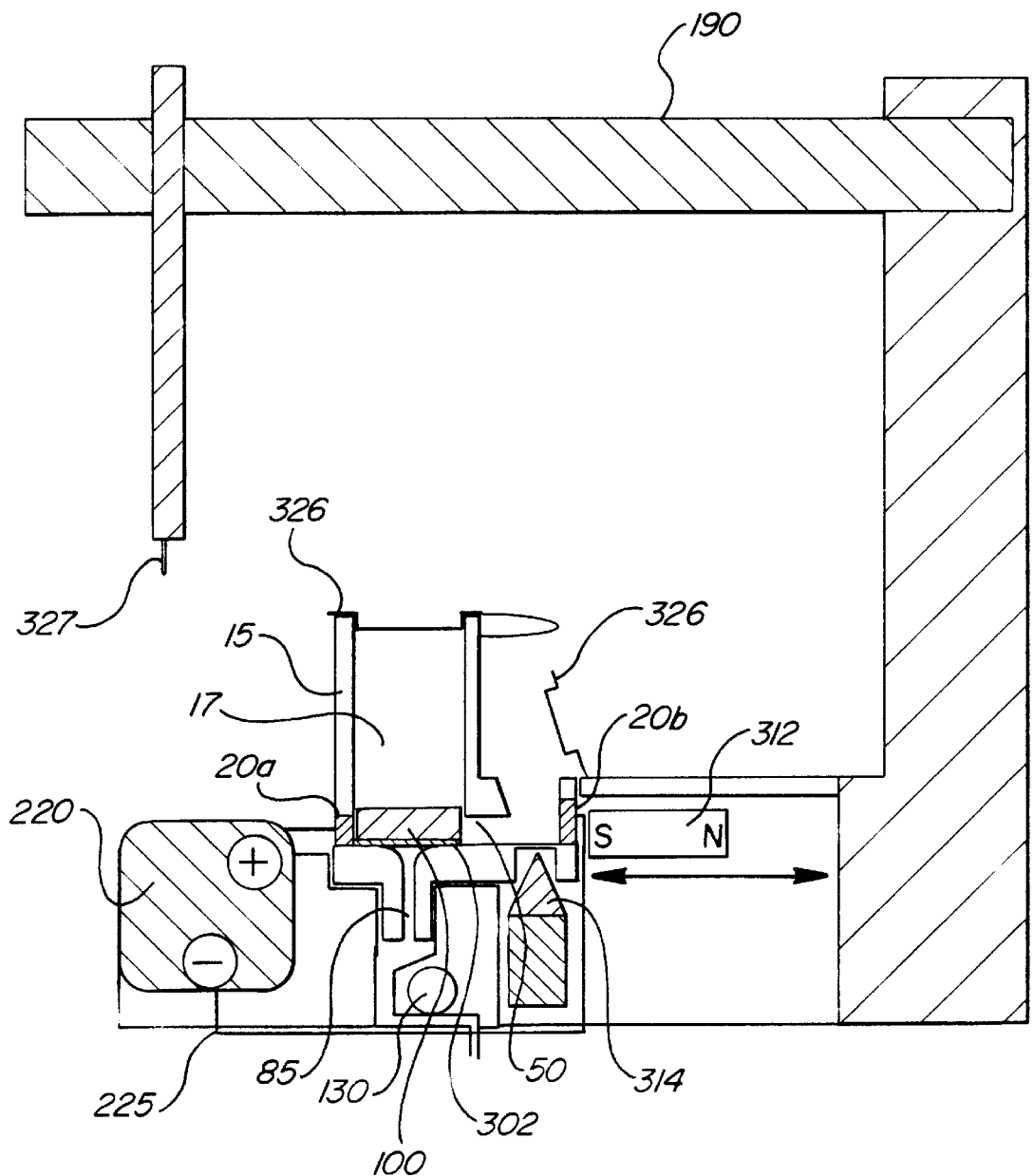

PROCESS AND DEVICE FOR ISOLATING NUCLEIC ACIDS

This application is a 371 of PCT/DE97/00517, filed Mar. 14, 1997, now abandoned.

BACKGROUND OF THE INVENTION

The invention relates to a process and an apparatus for isolating nucleic acids.

Before the analysis by polymerase chain reaction (PCR) of nucleic acids obtained from cells, it is necessary to purify and concentrate the nucleic acids. In addition, it can be necessary to remove from the sample to be analyzed certain substances interfering with the polymerase chain reaction, such as the hemoglobin prosthetic group.

In addition, in other techniques of nucleic acid analysis, for example hybridization, purification and concentration of the nucleic acids to be analyzed also plays an important role.

"Methods of Enzymology", Vol. 68, pp. 170–182, discloses using "spin-columns" for the isolation of nucleic acids. In a variant of this technique disclosed by DE 41 39 664 A1, the following working steps are used:

aa) cell disintegration, bb) adsorption of the nucleic acids to a glass fiber fleece in the presence of a high ionic strength buffer, and cc) elution of the nucleic acids by a low ionic strength buffer.

In the step aa), the liquid sample is passed through a glass fiber fleece to which the nucleic acids adsorb. The glass fiber fleece is then washed with various solutions. Finally, the nucleic acids are eluted from the solid phase in the presence of low ionic strength buffers.

The known process is disadvantageous in a number of respects: contamination of the sample can occur during washing of the solid phase. In addition, because of the capillary forces prevailing in the glass fiber fleece, the nucleic acids can only be partially recovered therefrom.

Furthermore, "Methods in Enzymology 65" (1980), pp. 371–380 discloses gel electrophoretic methods in which nucleic acids are bound to gels and are then brought back into solution by electroelution. Contamination of the solution can also occur in this case. The nucleic acids are present in the solution at high dilution. Concentration does not occur.

The object of the present invention is to specify a process and an apparatus by which the disadvantages of the prior art are avoided. In particular, a process and an apparatus for isolating nucleic acids which enable simple and inexpensive purification and concentration of nucleic acids are to be specified. Furthermore, a substantially automated isolation and concentration of nucleic acids is to be able to be carried out. Finally, the purpose of the invention is to avoid contaminations.

SUMMARY OF THE INVENTION

According to the invention, a process is provided for isolating nucleic acids from biological fluids and suspensions containing nucleic acids, a) the nucleic acids being bound to an adsorption medium, b) the nucleic acids being eluted from the adsorption medium, and c) being moved by electrophoresis from a reaction compartment into a removal compartment connected thereto and enriched there.

The process makes possible in a simple manner purification and concentration of nucleic acids from liquids. In particular in an automatic process procedure, the risk of contamination can be largely excluded. The elution can be performed by buffer change or electrically by electroelution or electrophoresis.

Further according to the invention, an apparatus for isolating nucleic acids from biological fluids and suspensions containing nucleic acids is provided, a reaction compartment for receiving an adsorption medium laden with nucleic acids being connected to a removal compartment, and the nucleic acids being able to be moved by an electrophoresis device from the reaction compartment into the removal compartment and enriched there. This apparatus makes a simple and inexpensive concentration and isolation of nucleic acids possible. By the provision of a separate removal compartment, contamination can be largely excluded.

Exemplary embodiments of the invention are described in more detail below with reference to the drawing.

BRIEF DESCRIPTION OF THE DRAWINGS

FIG. 6a shows a diagrammatic cross-section of a third exemplary embodiment of the apparatus, FIG. 6b shows a modification of the exemplary embodiment shown in FIG. 6a, FIG. 6c shows a diagrammatic cross-section of a fourth exemplary embodiment of the apparatus, FIG. 7a shows a bottom view of a fifth exemplary embodiment of the apparatus, FIG. 7b shows a plan view of the exemplary embodiment according to FIG. 7a, FIG. 7c shows a diagrammatic side view of the exemplary embodiment according to FIG. 7a, FIG. 7d shows a perspective view of a cover for a first exemplary embodiment of an elution apparatus, FIG. 7e shows a perspective view of the first exemplary embodiment of the elution apparatus without a cover, FIG. 7f shows a perspective view of the exemplary embodiment according to FIGS. 7a to 7c, FIG. 8 shows a diagrammatic cross-section through a sixth exemplary embodiment of the apparatus, FIG. 9 shows a diagrammatic cross-section through a coated electrode, FIG. 10 shows a diagrammatic cross-section through a seventh exemplary embodiment of the apparatus, FIG. 11 shows a diagrammatic cross-section through an eight exemplary embodiment of the apparatus, FIG. 12 shows a plan view of a second exemplary embodiment of an elution apparatus, and FIG. 13 shows a diagrammatic cross-section through a second exemplary embodiment of a purification and enrichment apparatus.

DETAILED DESCRIPTION OF THE PREFERRED EMBODIMENT

Figure 1:
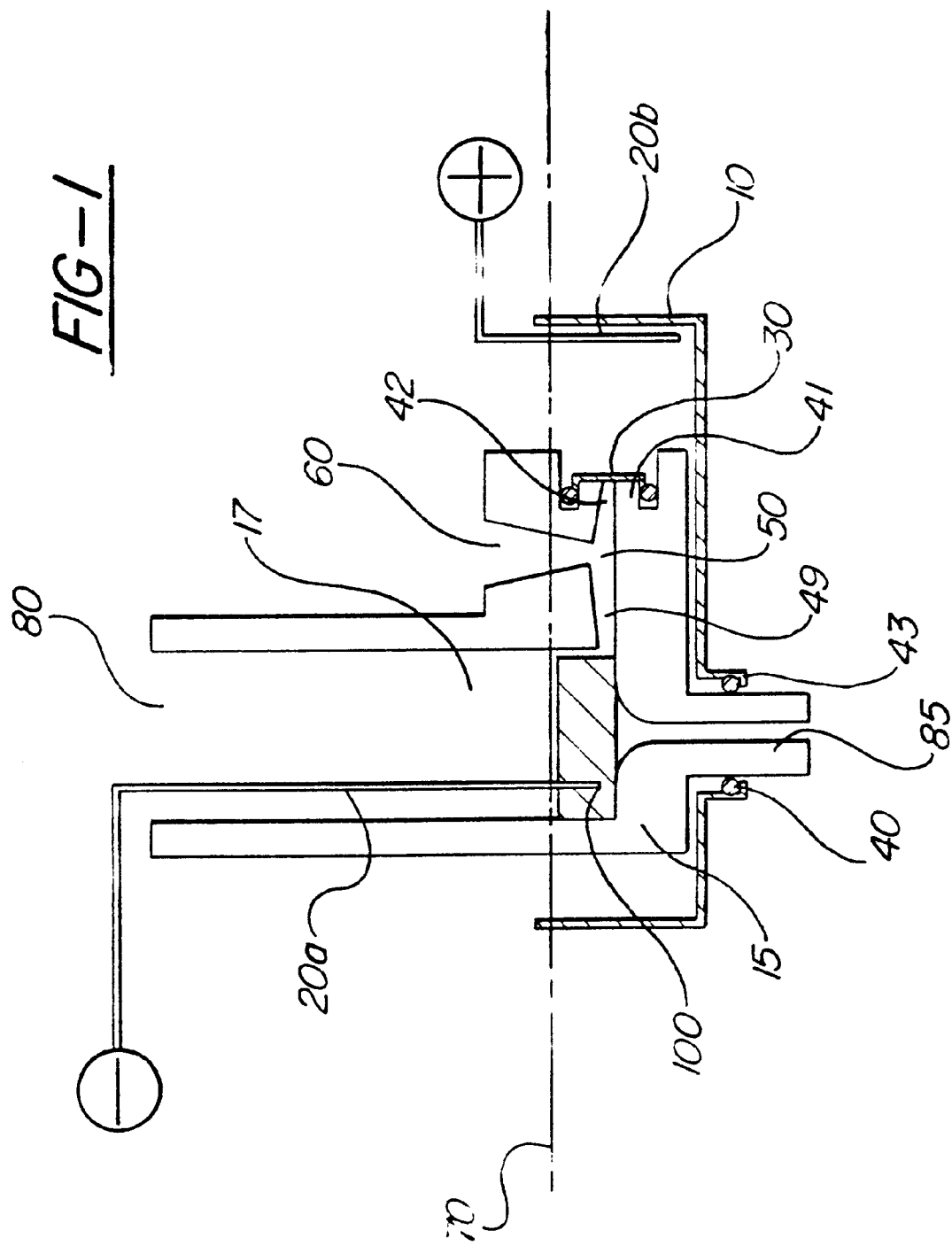
FIG. 1 shows a diagrammatic cross-section of a first exemplary embodiment of the apparatus.

FIG. 1 shows a diagrammatic cross-section of a first exemplary embodiment of the apparatus. A container 15 is held in an electrophoresis buffer tank 10 having a bottom-side breakthrough 43. The container 15 encloses a reaction compartment 17 which is connected via a channel 49 to a removal compartment 50. The volume of the reaction compartment 17 is preferably from 1 to 20 ml. The removal compartment 50 is in ion-conducting connection, by means of a first permeable membrane 30 sealing a first orifice 42, with an electrophoresis buffer held in the electrophoresis buffer tank 10. The volume of the removal compartment 50 is preferably from 0.005 to 0.1 ml. The first permeable membrane 30 is formed, for example, from a dialysis membrane which is impassable to nucleic acids, but is passable to salts, in particular chaotropic salts. The first permeable membrane 30 is fixed by a flexible ring, for example an O-ring, on a first nozzle 41. An adsorption medium 100, for example a glass fiber fleece, silica, glass beads, glass-encoated magnetic particles, anion exchanger or the like, is held in the reaction compartment 17. A cathode 20*a* projects through a second orifice 80 into the reaction compartment 17. An anode 20*b* dips into the electrophoresis buffer situated in the electrophoresis buffer tank 10, the level of which buffer is indicated by 70. Beneath the adsorption medium 100, a second nozzle 85 which passes through the breakthrough 43 extends from the container 15. The second nozzle 85 is sealed from the electrophoresis buffer tank 10 by an O-ring 40. The removal compartment 50 has a removal orifice 60. It is designed in such a manner that air inclusions are avoided. The removal compartment 50 can be designed, in particular, as capillary.

Figure 2:
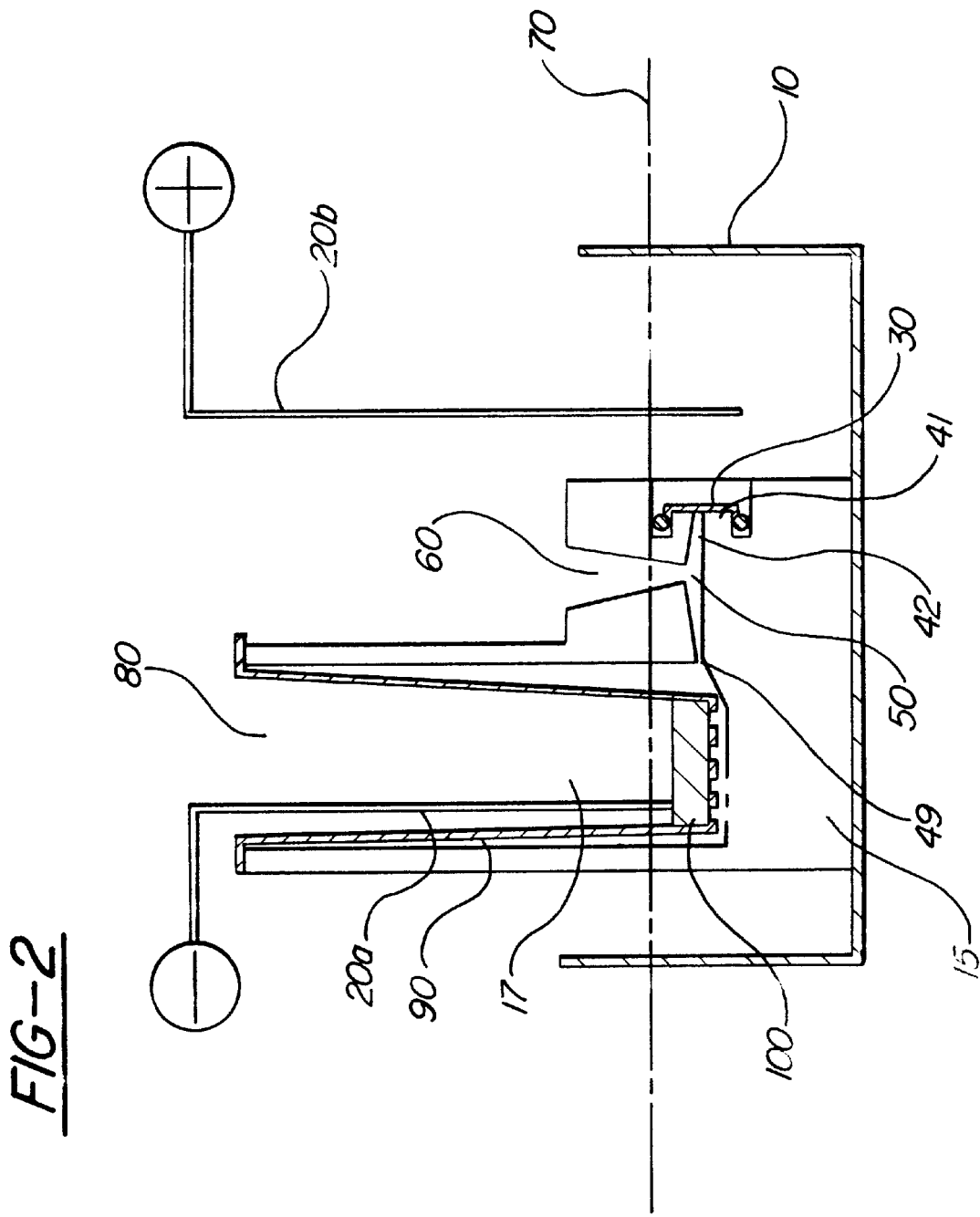
FIG. 2 shows the exemplary embodiment according to FIG. 1 with a "spin columns"

FIG. 2 essentially shows the first exemplary embodiment shown in FIG. 1. In this case a spin column 90 is held in the reaction compartment 17. The second nozzle 85 passing through the electrophoresis buffer tank 10 is not provided here.

Figure 3:
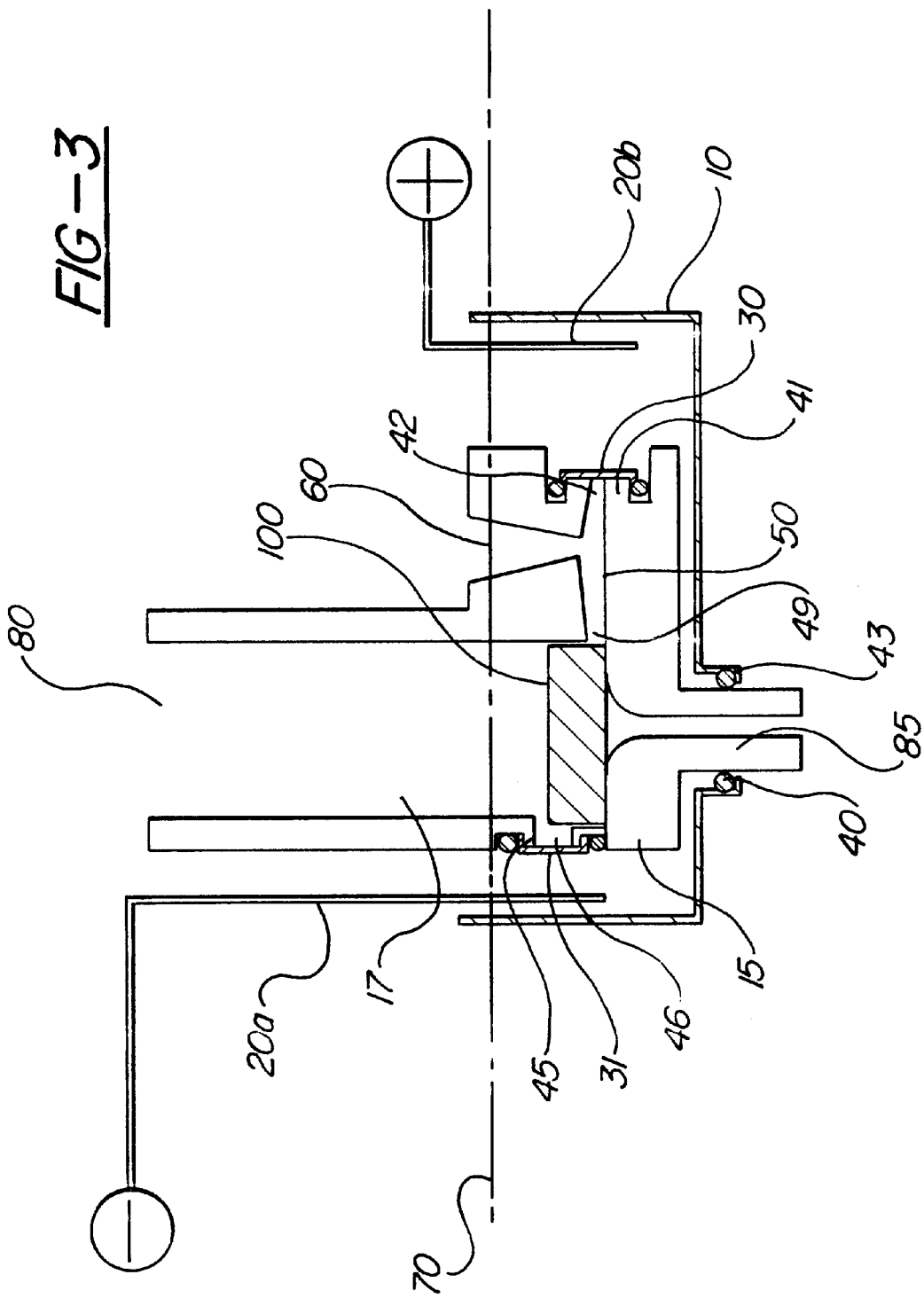
FIG. 3 shows a diagrammatic cross-section of a second exemplary embodiment of the apparatus.

FIG. 3 shows a diagrammatic cross-sectional view through a second exemplary embodiment of the apparatus. In this case the cathode 20*a* is situated outside the reaction compartment 17. It dips directly into the electrophoresis buffer tank 10. On the part of the container 15 surrounding the reaction compartment 17, a third nozzle 45 is provided, the third orifice 46 of which is sealed by a second permeable membrane 31.

Figure 4:
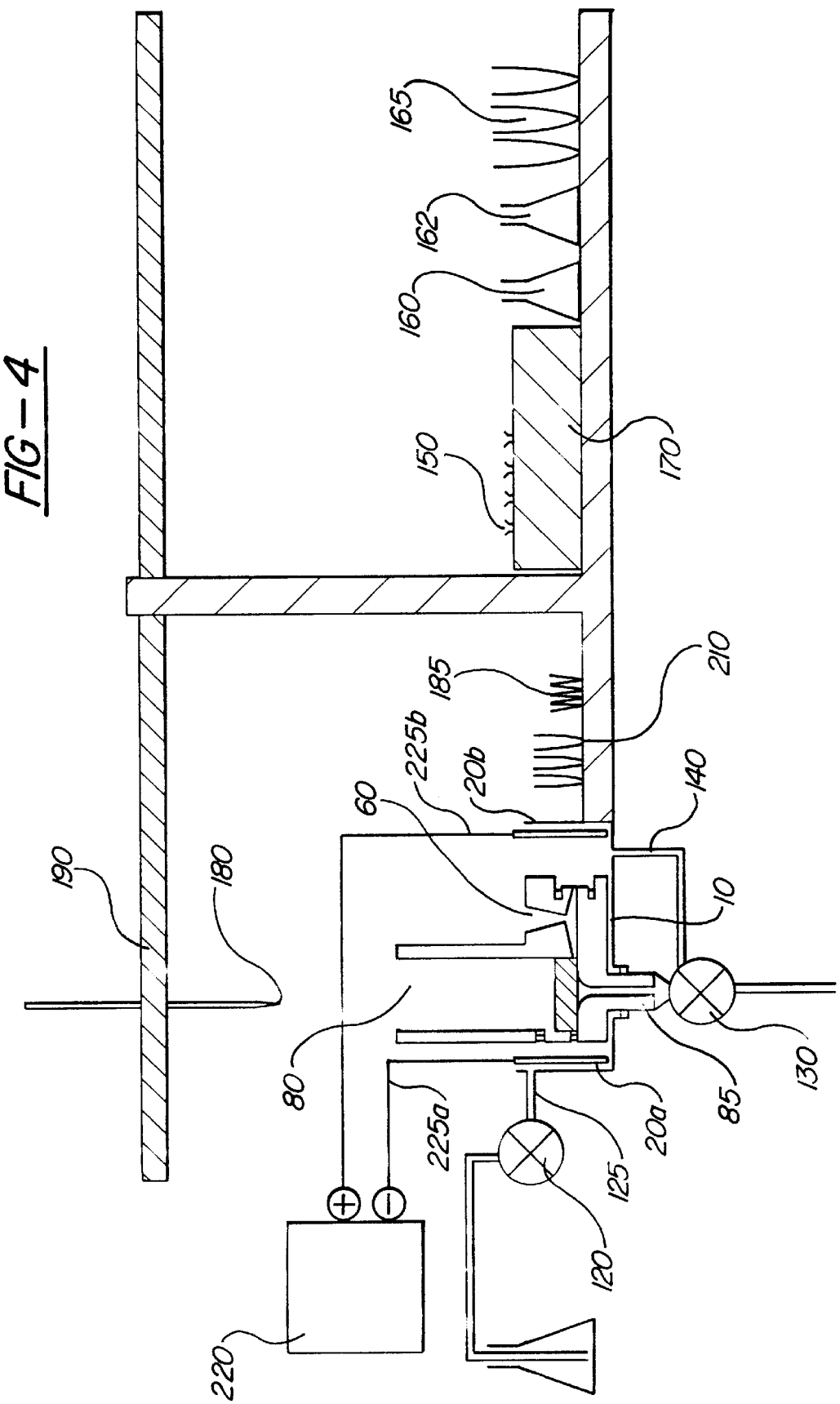
FIG. 4 shows a diagrammatic cross-section through a first exemplary embodiment of a purification and enrichment apparatus having an apparatus according to FIG. 3.

FIG. 4 shows a diagrammatic cross-sectional view through a first exemplary embodiment of a purification and enrichment apparatus having the apparatus according to FIG. 3. The apparatus according to FIG. 3 is situated in the area of action of an x,y,z pipettor, whose x,y,z pipetting arm is designated 190. The x,y,z pipetting arm 190 holds a pipetting tip 180, preferably a disposable tip. A suitable x,y,z pipettor is available from, for example, TECAN AG, Switzerland. In addition, a heatable shaker frame 170 is arranged in the area of action of the x,y,z pipettor. Reaction tubes 150 for the lysis are held in the shaker frame 170. Beside this there are situated a first vessel 160 for the lysis, a second vessel 162 for holding a wash solution and sample vessels 165. 185 designates a store of pipette tips and 210 indicates PCR vessels.

The electrophoresis buffer tank 10 is provided with a filling port 125, which is connected to an electrophoresis buffer reservoir 110, with intermediate connection of a pump 120. The second nozzle 85 and an outlet line 140 provided at the bottom of the electrophoresis buffer tank 10 are connected to a second pump 130. The second pump 130 is preferably constructed as a peristaltic pump. A suitable peristaltic pump is available, for example, from Cavro, California, USA. The cathode 20*a* and the anode 20*b* are connected via electrical leads 225*a* and 225*b* to a power supply 220. The first pump 120 and the second pump 130, the shaking frame 170, the x,y,z pipettor and the power supply 220 are constructed in such a way that they can be controlled by a process computer. Thus fully automatic operation of the purification and enrichment apparatus is possible.

Figure 5:
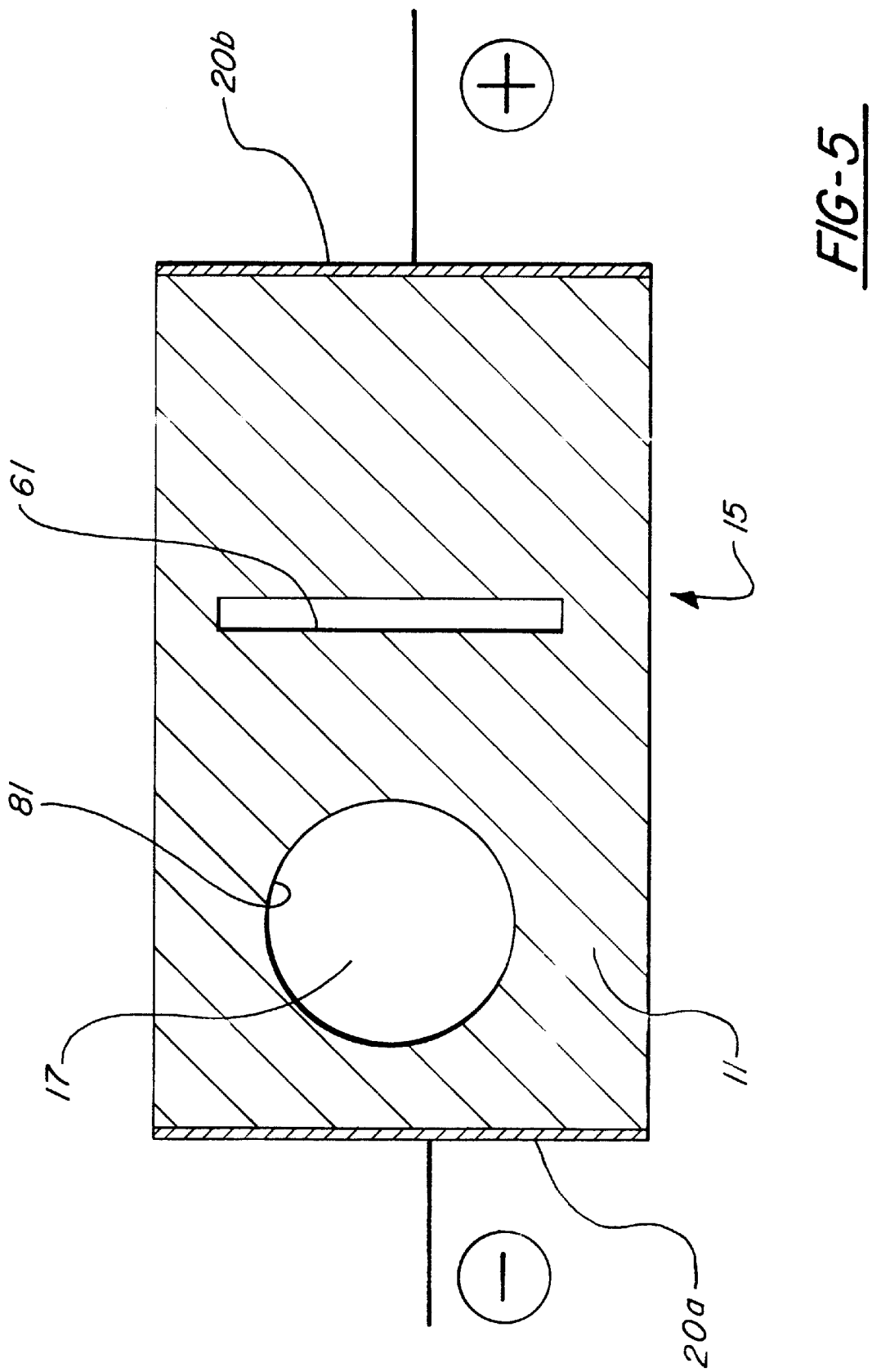
FIG. 5 shows a plan view of a flat bed agarose gel.

FIG. 5 shows a plan view of a particularly simple variant of a container 15. This is made from a flat bed agarose gel 11, on the opposite transverse sides of which lie the cathode 20*a* and the anode 20*b*. In the flat bed agarose gel 11 are provided a first recess 81 forming the reaction compartment 17 for holding adsorption medium and a second recess 61. The second recess 61 is formed as a slot. It serves for removing the nucleic acids enriched therein.

FIG. 6*a* shows a diagrammatic cross-section through a third exemplary embodiment of the apparatus. In this case the container 15 is constructed in the form of a cross-connection piece. The adsorption medium 100 is situated on a support fleece 302. The cathode 20*a* and the anode 20*b* are constructed as electrically conductive plastic pipette tips, which are connected to the electrophoresis buffer tank (not shown here). They are connected to the container 15 via tubing pieces 318. Nucleic acids accumulated in the removal compartment 50 can be taken off through the removal orifice 60.

As shown in FIG. 6*b*, further support fleeces 303 can be arranged between the removal compartment 50 and an intermediate compartment 321. In the fourth exemplary embodiment shown in FIG. 6*c*, the orifices of the electrodes 20*a* and 20*b* formed as plastic pipette tips are sealed.

In FIGS. 7*a* to 7*c*, a fifth exemplary embodiment of the apparatus is shown in several views. In this case, the container 15 comprises a rectangular component. The reaction compartment 17 is formed by a borehole. On both sides, next to the reaction compartment 17, recesses 320, 321 for holding the cathode 20*a* and the anode 20*b*, respectively, are provided. The wall between the recesses 320, 321 and the reaction compartment 17 is fabricated to be ion-conducting. The recesses 320 and 321 serve to hold electrophoresis buffer. They are sealed with stoppers 340. The electrophoresis buffer tank, in this embodiment, consists of two part-containers which enclose the reaction compartment 17. A multiplicity of such apparatuses, one of which FIG. 7*f* again shows in a perspective view, can be constituents of the first exemplary embodiment shown in FIGS. 7*d* and 7*e* of an elution apparatus. The elution apparatus essentially consists of a multiple compartment container 410 for holding a plurality of apparatuses according to FIG. 7*f*. The multiple compartment container 410 has a vacuum connection 401 and connections 402 for a liquid circuit for heating the elution apparatus. A cover 400 shown in FIG. 7*d* is provided with leads 226*a*, 226*b* for the electrodes.

FIG. 8 shows a sixth exemplary embodiment of the apparatus. In this case the cathode 20*a* is integrated into the wall of the reaction compartment 17 and the anode 20*b* is integrated into the opposite wall of the removal compartment 50. In the removal compartment 50, a permeable, in particular a semipermeable, membrane 310 is provided which is impermeable to nucleic acids. The membrane 310 prevents the nucleic acids from passing directly to the anode 20*b* and being destroyed there by redox processes. The adsorption medium 100 is supported by the support fleece 302 at the entry of the second nozzle 85.

FIG. 9 shows a diagrammatic cross-section through a coated electrode. A cathode or anode 20*a* or 20*b* fabricated from a noble metal, such as gold, silver or platinum, or electrically conductive plastic, is provided with a coating consisting of a plurality of layers. A first layer 323 applied to the noble metal or the plastic consists of biotinylated bovine serum albumin, a second layer 325 superposed thereupon consists of a streptavidin of polystreptavidin and an outer third layer 324 is formed of an oligonucleotide.

In the case of the seventh exemplary embodiment of the apparatus shown in FIG. 10, a movable permanent magnet 312 is arranged on the outside of the container 15 in such a manner that its north pole is in the vicinity of the cathode 20a. The reaction compartment 17 is sealed by a transparent snap-on cover 316. The removal compartment 50 is sealed by a snap-on cover 326 which is provided with a septum 328. The septum 328 can be pierced by a needle 327 for removal or addition of liquid. Thus contamination of the liquid present in the apparatus can be avoided. 314 designates a photomultiplier which is arranged above the transparent snap-on cover 316.

FIG. 11 shows a diagrammatic cross-section of an eighth exemplary embodiment. In contrast to the seventh exemplary embodiment, here, the movable permanent magnet 312 is arranged with its south pole in the vicinity of the outside of the anode 20b. The bottom of the removal compartment 50 is transparent. Opposite the removal orifice 60, the photomultiplier 314 is situated beneath the bottom of the removal compartment 50.

FIG. 12 shows a plan view of a second exemplary embodiment of an elution apparatus. In this case, a multiplicity of the apparatuses shown in FIG. 11 are arranged one beside the other. Thermostat plates 329, by which the temperature can be set, are provided on each of the longitudinal sides of the apparatuses.

FIG. 13 shows in diagrammatic cross-section a second exemplary embodiment of a purification and enrichment apparatus. In this case, the electrodes 20a and 20b of an apparatus according to FIG. 11 are connected to the power supply 220. The apparatus according to FIG. 11 is situated in the area of action of the x,y,z pipetting arm 190 of a robot x,y,z pipettor. The power supply 220, the second pump 130 for disposing of solutions to be discarded, an apparatus (not shown here) for moving the permanent magnet 312 and the robot x,y,z pipettor can be controlled fully automatically by a process computer, for example a personal computer.

The functioning of the described apparatuses is as follows:

Biological fluids which contain nucleic acids and are to be analyzed are brought into contact with the adsorption medium 100. In the course of this contact, the nucleic acids present in the solution are adsorbed to the adsorption medium 100. The nucleic-acid laden adsorption medium 100, for example the spin column 90, is inserted into the reaction compartment 17 through the second orifice 80. A direct current voltage in the range from 1 to 5000 V, preferably from 25 to 500 V, is then applied to the electrodes 20a, 20b. The negatively charged nucleic acids are detached as a result from the adsorption medium 100 and transported in the direction of the anode 20b arranged in the vicinity of the removal compartment 50. In order to avoid a direct contact of the nucleic acids with the anode 20b, the first permeable membrane 30 which is impassable to nucleic acids is provided. On account of the motion of the nucleic acids directed toward the anode 20b, these accumulate in the removal compartment 50. After an electrophoresis period of from 1 to 180 min, the current passed through the electrophoresis buffer is switched off. An elution volume comprising enriched nucleic acids can then be taken off through the removal orifice 60 of the removal compartment 50.

In order to avoid contamination, the removal orifice 60 can be sealed with the snap-on cover 326 which is provided with the septum 328. To remove elution volume, the septum 328 can be pierced by the needle 327.

Depending on the type of nucleic acids to be isolated, differently formed electrodes 20a, 20b can be used. The use of electrodes made from noble metal or conductive plastics, which electrodes can be coated, is suitable.

The apparatus according to the invention can be combined with a device for detecting chemiluminescence. For this purpose, the photomultiplier 314 is arranged in the vicinity of the container 15. The nucleic acids are first transported electrophoretically from the adsorption medium 100 toward the anode 20b. In the region of the anode 20b, an amplification of the nucleic acids, for example according to the polymerase chain reaction, can then be carried out. The amplified nucleic acids are then bound by addition of magnetic particles. By guiding the permanent magnet 312 to the anode 20b, the magnetic particles laden with nucleic acids are drawn to the anode 20b. After adding a chemiluminescence buffer and applying a voltage to the electrodes 20a, 20b, a chemiluminescence is initiated. The light emitted in this process is detected by the photomultiplier 314.

The abovementioned functions can be automated by a robot x,y,z pipettor. It is possible by this means to operate a multiplicity of the apparatuses according to the invention in succession automatically.

Nucleic acids can be isolated automatically using the purification and enrichment apparatuses shown in FIGS. 4 and 13. In this case, the following control program has proved to be expedient:

| Step No. | Equipment module | Working step |
|---|---|---|
| 1 | x,y,z pipettor | fetch pipette tip from store 185 |
| 2 | x,y,z pipettor | go to sample vessel 165 |
| 3 | x,y,z pipettor | take 210 µl of sample |
| 4 | x,y,z pipettor | go to reaction tube 150 |
| 5 | x,y,z pipettor | dispense 200 µl |
| 6 | x,y,z pipettor | discard pipette tip |
| 7 | x,y,z pipettor | fetch pipette tip from store 185 |
| 8 | x,y,z pipettor | go to first vessel 160 |
| 9 | x,y,z pipettor | take 710 µl of lysis reagent |
| 10 | x,y,z pipettor | go to reaction tube 150 |
| 11 | x,y,z pipettor | dispense 700 µl of lysis reagent |
| 12 | x,y,z pipettor | discard pipette tip |
| 13 | thermomixer | shake for 1 min |
| 14 | thermomixer | heat to 75° C. |
| 15 | controller | wait 10 min |
| 16 | thermomixer | cool to 25° C. |
| 17 | x,y,z pipettor | fetch pipette tip from store 185 |
| 18 | x,y,z pipettor | go to reaction tube 150 |
| 19 | x,y,z pipettor | take 810 µl of lysis mixture |
| 20 | x,y,z pipettor | go to second opening 80 |

-continued

| Step No. | Equipment module | Working step |
|---|---|---|
| 21 | x,y,z pipettor | dispense 800 µl of lysis mixture |
| 22 | x,y,z pipettor | discard pipette tip |
| 23 | pump (130) | pump lysis mixture through adsorption medium and discard |
| 24 | x,y,z pipettor | fetch pipette tip from store 185 |
| 25 | x,y,z pipettor | go to second vessel 162 |
| 26 | x,y,z pipettor | take 710 µl of wash reagent |
| 27 | x,y,z pipettor | go to second opening 80 |
| 28 | x,y,z pipettor | dispense 700 µl of wash solution |
| 29 | x,y,z pipettor | discard pipette tip |
| 30 | second pump 130 | pump wash solution through adsorption medium and discard |
| 31 | first pump 120 | pump electrophoresis buffer into the tank |
| 32 | x,y,z pipettor | fetch pipette tip from store 185 |
| 33 | x,y,z pipettor | go to electrophoresis buffer reservoir 110 |
| 34 | x,y,z pipettor | take 250 µl of electrophoresis buffer |
| 35 | x,y,z pipettor | go to second opening 80 |
| 36 | x,y,z pipettor | discard pipette tip |
| 37 | power supply 220 | apply voltage to electrodes 20a, 20b |
| 38 | controller | wait 20 min |
| 39 | x,y,z pipettor | fetch pipette tip from store 185 |
| 40 | x,y,z pipettor | take 60 µl of isolated nucleic acid from removal orifice 60 |
| 41 | x,y,z pipettor | go to PCR vessels 210 |
| 42 | x,y,z pipettor | dispense 50 µl into PCR vessels 210 |
| 43 | x,y,z pipettor | discard pipette tip |
| 44 | second pump 130 | pump electrophoresis buffer from the tank and discard |

EXAMPLE 1

Work-up of a whole blood sample with spin column and electrophoresis:

All reagents are taken from the QIAamp™ Blood Kit (Cat. No. 29104) from Qiagen, Hilden. After lysis and adsorption of the nucleic acid, in accordance with the manufacturer's procedure, the glass fiber fleece was taken out of the QIAamp spin column and placed in a specially prepared flat bed agarose gel in accordance with FIG. 5. The first recess 81 serves for holding the glass fleece and the second recess 61 is filled with electrophoresis buffer. In this manner, the nucleic acid can be eluted from the glass fleece electrophoretically and transferred into the subsequent agarose gel and the second recess 61. The isolated concentrated nucleic acid was removed from the second recess 61.

EXAMPLE 2

Work-up of a plasma sample

All reagents are taken from the QIAamp™ Blood Kit (Cat. No. 29104) from Qiagen, Hilden. For the work-up, the glass fiber fleece was removed from the QIAamp spin column and inserted into the apparatus according to FIG. 1 in such a manner that it was positioned at the bottom outlet. The volume of the entire reaction vessel was 2 ml. 200 µl of plasma were processed in accordance with the manufacturer's operating instructions. Instead of centrifugation, suction using an Eppendorf diaphragm pump was used. For the electrophoretic elution, an electrophoresis buffer described by Andrews A. T. (Andrew A. T.: Electrophoresis, Clarendon Press, Oxford, 1985, p. 160) was used. The permeable membrane used was dialysis tubing from Neolab, Heidelberg (catalogue No.: 2-9022). As electrodes 20a, 20b, use was made of wires 0.3 mm in diameter of a platinum/ruthenium alloy and as a power source, the electrophoresis power source from Hölzel, Dorfen, was used. 30 µl of elution volume containing the nucleic acid were removed from the removal orifice 60.

EXAMPLE 3

Isolation of DNA from chicken blood

Whole blood was collected from the carotid artery from a freshly slaughtered white fattening chicken and immediately admixed with ethylenediaminetetraacetic acid (Sigma, Munich, catalogue No. E-5513) at a concentration of 0.06 g of EDTA/ml of whole blood. The EDTA/whole blood was frozen in portions and stored at −15° C. All the reagents are taken from the "High Pure PCR Template Preparation Kit" from Boehringer Mannheim (catalogue No. 1 796 828). 100 µl of EDTA/whole blood (see above) were mixed with 200 µl of lysis buffer and 60 µl of proteinase K, in each case from the abovementioned reagent set, and incubated for 15 min at 70° C. After cooling to room temperature, 100 µl of isopropanol (Roth, Karlsruhe, catalogue No. 9866) are added and the mixture is shaken vigorously. The viscous reaction mixture is then sucked through the glass fleece using a vacuum pump (Eppendorf, Hamburg, No. 4151). The fleece was then washed five times with 500 µl of wash buffer (from kit, see above) containing 80% ethanol (Roth, Karlsruhe, catalogue No. 5054). The fleece was then removed from the filter tube and transferred into an apparatus according to FIG. 5, into the first recess 81. Approximately 0.5 ml of electrophoresis buffer (10 mM tris-HCl [Sigma, Munich catalogue No. T-8529] 5 mM sodium acetate [Sigma, Munich catalogue No. S-3272] 0.5 mM EDTA [see above] pH 8.2) were then pipetted onto the fleece into the first recess 81 which buffer had previously been heated to 70° C. Thereafter, the electroelution was performed by applying a direct current voltage of a maximum of 10 mA at approximately 60° C. The power supply used was an electrophoresis transformer from Hölzel, Dorfen (No. 0628/1985). The eluate was collected in fractions 1–7, after a defined time (10–15 min) fractions of approximately 50 µl being taken and collected from the orifice (61) using an Eppendorf pipette. The fractions were analyzed on an agarose gel (0.05 mg of agarose in 60 ml of electrophoresis buffer containing 40 µl of ethidium bromide solution (100 mg of ethidium bromide [Sigma, Munich No. E-8751] in distilled water)). 40 µl of lysis mixture were used as control. The control and fractions after electroelution for 15 min showed a fluorescent band after electrophoresis of 5 min at approximately 40 V and a maximum of 50 mA with illumination under a UV lamp from Roger Electronic Products (No. MD-1782GS). The power supply used was an electrophoresis transformer from Hölzel, Dorfen (No. 0628/1985).

EXAMPLE 5

Production of a coated electrically conductive plastic electrode (FIG. 9)

Biotinylated bovine immunoglobulin G (B-IgG) was first prepared. For this purpose, 0.5 ml of a B-IgG solution (2 mg of B-IgG [Boehringer Mannheim Cat. No. 1293621103] in 1 ml of PBS ($NaH_2PO_4.1H_2O$ 2.76 g/l; $NA_2HPO_4.2H_2O$ 3.56 g/l; NaCl 8 g/l; pH 7.25)) was mixed with 6 μl of D-biotinoyl-ε-aminocaproic acid N-hydroxysuccinimide ester solution in PBS and DMSO (batch in accordance with Biotin Labeling Kit from Boehringer Mannheim catalogue No. 1418165) and stirred for 2.5 h at room temperature on a magnetic stirrer and then allowed to stand overnight. The molar ratio of biotin:B-IgG is 20:1 in this batch.

To coat electrically conductive plastic with biotinylated B-IgG, disks of 4 mm in diameter were cut from a blank piece produced in the injection molding process from PRE-ELEC TP 4474 (Premix Oy, Finland), placed in a well of an uncoated microtiter plate and washed three times in a solution of 0.2 ml of coating buffer ($NaHCO_3$ 4.2 g/l; pH 9.6), then in a solution of 40 ml of coating buffer ($NAHCO_3$ 4.2 g/l; pH 9.6) and 6 μl of B-IgG biotin solution. Coating was performed overnight.

The disks are then washed three times each time with 100 ml of milli-Q water, the solid and liquid phases being separated by sedimentation or centrifugation. The disks are then taken up in 40 ml of PBS again.

EXAMPLE 6

Performing a sample preparation with electroelution, amplification and electrochemiluminescence measurement for detection of material amplified by PCR The apparatus shown in FIG. 14, to carry out the isolation, amplification and chemiluminescence measurement, was automatically controlled by a computer program having the following program steps:

| Process modules | Individual steps |
| --- | --- |
| Sample preparation | |
| Lysis | pipette sample, lysis mixture, proteinase K into reaction compartment 17 |
| | close reaction compartment 17 |
| | heat reaction compartment 17 to 70° C. |
| | cool reaction compartment 17 to room temperature |
| | open reaction compartment 17 |
| | add isopropanol |
| | draw off reaction mixture from reaction compartment 17 by suction through second nozzle 85 |
| Electroelution | add elution buffer |
| | apply voltage to electrodes 20a, 20b |
| | nucleic acid migrates into the removal compartment 50 |
| Amplification | addition of PCR mix to the removal compartment 50 |
| | closure of the second nozzle 85, second orifice 80 and removal orifice 60 |
| | cyclic heating and cooling of the removal compartment 50 |
| Denaturation | opening the removal orifice 60 |
| Probe annealing | addition of RU probe |
| | closure of removal orifice 60 |
| | heating and cooling of the removal compartment 50 |
| Detection | opening removal orifice 60 |
| | addition of SA magnetic particles through removal orifice 60 |
| | closure of removal orifice 60 |
| Magnetic separation | applying permanent magnet 312 with magnetic field for the removal compartment 50 |
| — | drawing off reaction mixture from the removal compartment 50 by suction |

-continued

| Process modules | Individual steps |
| --- | --- |
| Wash magnetic particles (option) | addition of wash solution through removal orifice 60 |
| | removal of the magnetic field for the removal compartment 50 |
| | drawing off the wash solution by suction through the second nozzle 85 |
| | addition of assay buffer through removal orifice 60 |
| Electro-chemiluminescence measurement | applying voltage to the electrodes 20a, b |
| | luminescence measurement by photomultiplier 314 |

List of designations 10 electrophoresis buffer tank
11 flat bed agarose gel
15 container
17 reaction compartment
20a cathode
20b anode
30 first permeable membrane
31 second permeable membrane
40 O-ring
41 first nozzle
42 first orifice
43 breakthrough
44 second nozzle
45 third nozzle
46 third orifice
49 channel
50 removal compartment
60 removal orifice
61 second recess
70 filling level
80 second orifice
81 first recess
85 second nozzle
90 spin column
100 adsorption medium
110 electrophoresis buffer reservoir
120 first pump
125 filling port
130 second pump
140 outlet line
150 reaction tube
160 first vessel
162 second vessel
165 sample vessel
170 shaker frame
180 pipette tip
185 store of pipette tips
190 x,y,z pipetting arm
210 PCR vessels
220 power supply
225a,b electrical leads
302 support fleece
303 further support fleece
310 semipermeable membrane
312 permanent magnet
313 magnetic particles
314 photomultiplier
316 transparent snap-on cover
318 tubing piece 320,321 recesses
323 first layer
324 third layer
325 second layer
326 snap-on cover
327 needle
328 septum
329 heating plates
340 stopper
400 cover
401 vacuum connection
402 connections
410 multiple compartment container

I claim:

1. An apparatus for the contamination-free isolation of nucleic acids from biological fluids and suspensions containing nucleic acids comprising:
a reaction compartment for holding an adsorption medium laden with nucleic acids; connected via a channel to a removal compartment; wherein the nucleic acids can be moved by an electrophoresis device from the reaction compartment into the removal compartment and enriched there; and the reaction compartment can be charged via a charging orifice and drained via a draining orifice which is located essentially opposite of the charging orifice.

2. The Apparatus according to claim 1, wherein the reaction compartment (17) is surrounded by an electrophoresis buffer tank (10).

3. The Apparatus according to claim 2, wherein the reaction compartment (17) is connected to the electrophoresis buffer tank (10) in an ion-conducting manner.

4. The Apparatus according to claim 2, wherein the reaction compartment (17) is situated in the electrophoresis buffer tank (10).

5. The Apparatus according to claim 1, wherein the reaction compartment (17) can be charged and drained via at least one orifice (80).

6. The Apparatus according to claim 1, wherein an adsorption medium (100) for nucleic acids that is held in the reaction compartment (17).

7. The Apparatus according to claim 1, further comprising the ion-conducting connection that is formed by at least one permeable membrane (31) which retains nucleic acids.

8. The Apparatus according to claim 1, wherein the apparatus is fabricated from thermoplastic.

9. The Apparatus according to claim 1, wherein the electrophoresis device has at least two electrodes (20a, 20b) of which at least one projects into the electrophoresis buffer tank (10) or is a component of the same.

10. The Apparatus according to claim 1, wherein the electrophoresis device has at least two electrodes (20a, 20b), of which at least one projects into the removal compartment (50) or is a component of a container (15) enclosing the removal compartment (50).

11. The Apparatus according to claim 9, wherein one of the electrodes (20a, 20b) projects into the reaction compartment (17) or is a component of the container (15) enclosing the reaction compartment (17).

12. The Apparatus according to claim 9, wherein at least one of the electrodes (20a, 20b) is fabricated from an electrically conducting plastic.

13. The apparatus according to claim 12, wherein the electrically conductive plastic is an electrically conductive additive, selected from the group consisting of graphite, iron, silver and other metals.

14. The apparatus according to claim 9, wherein the resistance of the at least two electrodes (20a, 20b) is less than 100 MΩ.

15. The apparatus according to claim 9, wherein the at least two electrodes (20a, 20b) have a coating.

16. The apparatus according to claim 9, wherein the coating of the at least two electrodes (20a, 20b) consists of a plurality of layers (323, 324, 325).

17. The apparatus according to claim 16, further comprising at least one layer formed from a biological polymer, optionally a protein capable of binding.

18. The Apparatus according to claim 17, wherein the protein capable of binding is an antibody, an antigen or a component of another ligand-receptor pair.

19. The Apparatus according to claim 17, wherein the biological polymer is of a type such that nucleic acids can bind thereto.

20. The Apparatus according to claim 17, wherein the biological polymer is an oligonucleotide.

21. The Apparatus according to claim 17, wherein the biological polymer is a protein-like amino acid construct (PNA construct).

22. The Apparatus according to claim 16, wherein one of the layers (323, 324, 325) consists of chemically reactive linker molecules.

23. The apparatus according to claim 9, wherein the at least two electrodes (20a, 20b) are provided opposite each other in the wall of the container (15).

24. The Apparatus according to claims 1, further comprising means (312) for producing a magnetic field which can be switched on and off arranged in such a manner that the container (15) can be penetrated by the magnetic field.

25. The Apparatus according to claim 1, further comprising in the vicinity of the container (15) a detection device, preferably a photomultiplier (314), is arranged.

26. The Apparatus according to claim 25, wherein the container (15) has an optical window (316).

27. The elution apparatus having a plurality of apparatuses according to one of claims 1 to 26, wherein the electrodes (20a, 20b) assigned to the apparatuses are electrically connected to one another and to a power supply (220).

28. The elution apparatus according to claim 27, wherein the apparatuses are arranged geometrically in the 96-well microtitration plate format.

29. A purification and enrichment apparatus having an apparatus according to claim 1 or an elution apparatus according to claim 27, wherein at least one of the following devices is provided:

x,y,z-pipetting arm (190)

thermostated shaker frame (170)

heating/cooling medium (329) for the cyclic heating and cooling, power supply (220), at least two electrodes (20a, 20b), at least one pump (120, 130), at least one magnet (312), at least one photomultiplier (314).

30. The purification and enrichment apparatus as claimed in claim 29, characterized in that the apparatus, the elution apparatus and the device(s) can be automatically controlled by means of a process computer for carrying out the process of isolating nucleic acids from biological fluids and suspensions containing nucleic acids wherein
a) the nucleic acids are bound to an adsorption medium (100),
b) the bound nucleic acids are eluted from the adsorption medium (100) and
c) the eluted nucleic acids are moved by electrophoresis from the reaction compartment (17) into the connected removal compartment (50) and enriched therein.

* * * * *

UNITED STATES PATENT AND TRADEMARK OFFICE
CERTIFICATE OF CORRECTION

PATENT NO.  : 6,071,395
DATED       : June 6, 2000
INVENTOR(S) : Lange

It is certified that error appears in the above-identified patent and that said Letters Patent is hereby corrected as shown below:

Column 11,
Line 37, delete "wherein" and insert -- further comprising --.
Line 41, delete "the" and insert -- an --.

Column 12,
Line 29, delete ", is arranged".

Signed and Sealed this

Thirteenth Day of November, 2001

Attest:

NICHOLAS P. GODICI
Attesting Officer
Acting Director of the United States Patent and Trademark Office